United States Patent
Kim et al.

(10) Patent No.: US 11,458,152 B2
(45) Date of Patent: Oct. 4, 2022

(54) USE OF AGAROBIOSE OR AGAROOLIGOSACCHARIDE HAVING ANTICARIOGENIC ACTIVITY

(71) Applicant: Korea University Research and Business Foundation, Seoul (KR)

(72) Inventors: Kyoung Heon Kim, Seoul (KR); Eun-Ju Yun, Seoul (KR); Sora Yu, Namyangju-si (KR); Dong-Hyun Kim, Busan (KR); Sang-Hyun Lee, Daejeon (KR); Jung Yeon Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 135 days.

(21) Appl. No.: 16/985,850

(22) Filed: Aug. 5, 2020

(65) Prior Publication Data

US 2020/0376012 A1     Dec. 3, 2020

Related U.S. Application Data

(62) Division of application No. 16/349,885, filed as application No. PCT/KR2017/012914 on Nov. 15, 2017.

(30) Foreign Application Priority Data

Nov. 15, 2016  (KR) .................. 10-2016-0152163
Feb. 3, 2017  (KR) .................. 10-2017-0015459

(51) Int. Cl.

| | |
|---|---|
| *A61K 8/73* | (2006.01) |
| *A61Q 11/00* | (2006.01) |
| *A61K 31/702* | (2006.01) |
| *A23L 33/125* | (2016.01) |
| *A61P 1/02* | (2006.01) |
| *A61P 31/04* | (2006.01) |
| *A61K 8/60* | (2006.01) |
| *A61K 9/00* | (2006.01) |
| *A61K 31/7016* | (2006.01) |
| *A61K 31/729* | (2006.01) |

(52) U.S. Cl.
CPC .......... *A61K 31/702* (2013.01); *A23L 33/125* (2016.08); *A61K 8/60* (2013.01); *A61K 8/73* (2013.01); *A61K 9/0056* (2013.01); *A61K 31/7016* (2013.01); *A61K 31/729* (2013.01); *A61P 1/02* (2018.01); *A61P 31/04* (2018.01); *A61Q 11/00* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,502,181 A | 3/1996 | Kojima et al. | |
| 2007/0202238 A1* | 8/2007 | Enoki ................. | A23L 7/109 426/590 |

FOREIGN PATENT DOCUMENTS

| | | | |
|---|---|---|---|
| JP | 2002-029952 | * | 1/2002 |
| JP | 2002-029952 A | | 1/2002 |
| JP | 2014-114282 A | | 6/2014 |
| KR | 10-2001-0018802 A | | 3/2001 |
| KR | 10-2007-0038182 A | | 4/2007 |

OTHER PUBLICATIONS

International Search Report of PCT/KR2017/012914 dated Feb. 13, 2018 [PCT/ISA/210].
L. Trahan et al., "Selection for *Streptococcus mutans* with an Altered Xylitol Transport Capacity in Chronic Xylitol Consumers", J Dent Res, May 1987, pp. 982-988, vol. 66, No. 5.
L. Trahan et al., "Transport and Phosphorylation of Xylitol by a Fructose Phosphotransferase System in *Streptococcus mutans*", Caries Res., 1985, pp. 53-63, vol. 19.
Stuart G. Dashper et al., "Lactic acid excretion by *Streptococcus mutans*", Microbiology, 1996, pp. 33-39, vol. 142.
W. J. Loesche et al., "Association of *Streptococcus mutans* with Human Dental Decay", Infection and Immunity, Jun. 1975. pp. 1252-1260, vol. 11, No. 6.

* cited by examiner

*Primary Examiner* — Brian Gulledge
(74) *Attorney, Agent, or Firm* — Sughrue Mion, PLLC

(57) ABSTRACT

The present invention relates to a use of an agarobiose or agarooligosaccharides having anticariogenic activity. More specifically, a lower concentration of agarobiose or agarooligosaccharides than the concentration of xylitol suppresses the growth of *Streptococcus mutans* and suppresses acid production, and thus can be used for anti-cariogenic purposes.

4 Claims, 4 Drawing Sheets

USE OF AGAROBIOSE OR AGAROOLIGOSACCHARIDE HAVING ANTICARIOGENIC ACTIVITY

CROSS-REFERENCE TO RELATED APPLICATIONS

This application is a divisional application of U.S. application Ser. No. 16/349,885, filed May 14, 2019, which is a National Stage of International Application No. PCT/KR2017/012914, filed Nov. 15, 2017, claiming priorities to Korean Patent Application No. 10-2016-0152163, filed Nov. 15, 2016 and Korean Patent Application No. 10-2017-0015459, filed Feb. 3, 2017, the disclosures of which are incorporated herein by reference in their entireties.

BACKGROUND

1. Field of the Invention

The present invention relates to a use of agarobiose or agarooligosaccharides having an anticariogenic activity.

2. Discussion of Related Art

Dental caries is one of the main causes of people visiting dentists and its incidence rate has increased due to the use of sugar as a sweetener in modern society. *Streptococcus mutans* is a major causative bacterium of dental caries (Loesche W J et al. (1975) *Infect Immun.* 11(6): 1252-60). *Streptococcus mutans*, which is a bacterium that resides in the human mouth, breaks sugar down, and secretes a glucosyltransferase (GTF) to form insoluble glucans on the tooth surface. *Streptococcus mutans* or various other bacteria are attached to the tooth surface to proliferate thereon. Bacteria on the tooth surface cause tooth decay as the enamel of the tooth surface is damaged by an organic acid such as lactic acid, which is a carbohydrate metabolite (Dashper S. G., et al. (1996) *Microbiol.* 142, 33-29). As representative materials for preventing dental caries by reducing the number of *Streptococcus mutans* in dental plaque, there are fluoride compounds and xylitol (Trahan L et al (1985) *Caries Res.* 19: 53-63). Xylitol, which is a 5-carbon alcohol present in nature, has sweetness similar to sugar and a sense of refreshment thereof. Due to these merits, xylitol is currently produced as gum, toothpastes, and the like and widely used, but it is disadvantageous in that the growth of *Streptococcus mutans* can be suppressed only in the case of including xylitol at a high concentration.

Currently, research into natural materials having antimicrobial activity against *Streptococcus mutans* is increasingly conducted and there is a growing interest in natural sugars as an anti-cariogenic sweetener. However, research results on natural sugars which have an anticariogenic effect as much as xylitol are insufficient. When *Streptococcus mutans* ingests xylitol, xylitol-5-phosphate is formed by a phosphoenolpyruvate-xylitol phosphotransferase system (PEP-xylitol PTS). This inhibits the activity of a glycolytic enzyme and metabolism of xylitol no longer occurs, which is then extracellularly excreted. Through this process, bacterial growth and acid production are inhibited via a futile cycle that does not generate energy and only consumes energy. At this time, the growth of *Streptococcus mutans* can be inhibited only with xylitol having a concentration of 10 g/L or higher, and studies have also shown that resistant strains, the growth of which is not inhibited by xylitol, are produced when *Streptococcus mutans* is continuously cultured in a xylitol-containing medium (Trahan L et al (1985) *Caries Res.* 19: 53-63, Trahan L et al (1987) *J Dent Res.* 66: 982-988).

SUMMARY OF THE INVENTION

An object of the present invention is to provide an anticariogenic use of agarobiose or agarooligosaccharides.

To achieve the above technical object, the present invention provides a pharmaceutical composition for preventing or treating an oral disease, which includes one or more selected from the group consisting of agarobiose and agarooligosaccharides.

The present invention also provides a use of agarobiose or agarooligosaccharides for preparing a pharmaceutical composition for preventing or treating an oral disease.

The present invention also provides a method of preventing or treating an oral disease which includes administering a pharmaceutical composition for preventing or treating an oral disease to a subject.

The present invention also provides an oral hygiene composition for preventing or alleviating an oral disease, which includes one or more selected from the group consisting of agarobiose and agarooligosaccharides.

The present invention also provides a food composition for preventing or alleviating an oral disease, which includes one or more selected from the group consisting of agarobiose and agarooligosaccharides.

The agarooligosaccharides may be obtained from an acid hydrolysate of agarose. More particularly, the agarooligosaccharides may be obtained by reacting agarose with a 0.1% (w/v) to 5% (w/v) strong acid at 80° C. to 140° C. for 5 minutes to 30 minutes and adding a strong base to the resulting reaction product to be neutralized to a pH of 5 to 6.

The strong acid may be selected from the group consisting of phosphoric acid, sulfuric acid, hydrochloric acid, and nitric acid.

The neutralization process may be performed by adding a strong base to the strong acid-treated agarose to adjust a pH thereof to 5 to 6.

The strong base may be selected from the group consisting of NaOH, KOH, Ca(OH)$_2$, and Ba(OH)$_2$.

The agarooligosaccharides may be a mixture of agarobiose, agarotetraose, agarohexaose, and agarooctaose.

The agarobiose may be obtained by separating and purifying an acid hydrolysate of agarose through gel permeation chromatography.

The agarobiose or agarooligosaccharides may inhibit the growth of *Streptococcus mutans*, which is an oral bacterium, and the production of acid by carbon source consumption of *Streptococcus mutans*.

The oral disease may be any one selected from the group consisting of dental caries, gingivitis, periodontitis, oral mucous ulcers, halitosis, and xerostomia.

Agarobiose or agarooligosaccharides of the present invention has been verified to inhibit the growth and acid production of *Streptococcus mutans*, and thus is anticipated to be applied to the development field of oral hygiene products such as toothpastes, mouthwashes, oral sprays, and the like, foods such as gum, candies, and the like, and medicines.

DETAILED DESCRIPTION OF EXEMPLARY EMBODIMENTS

Figure 1:
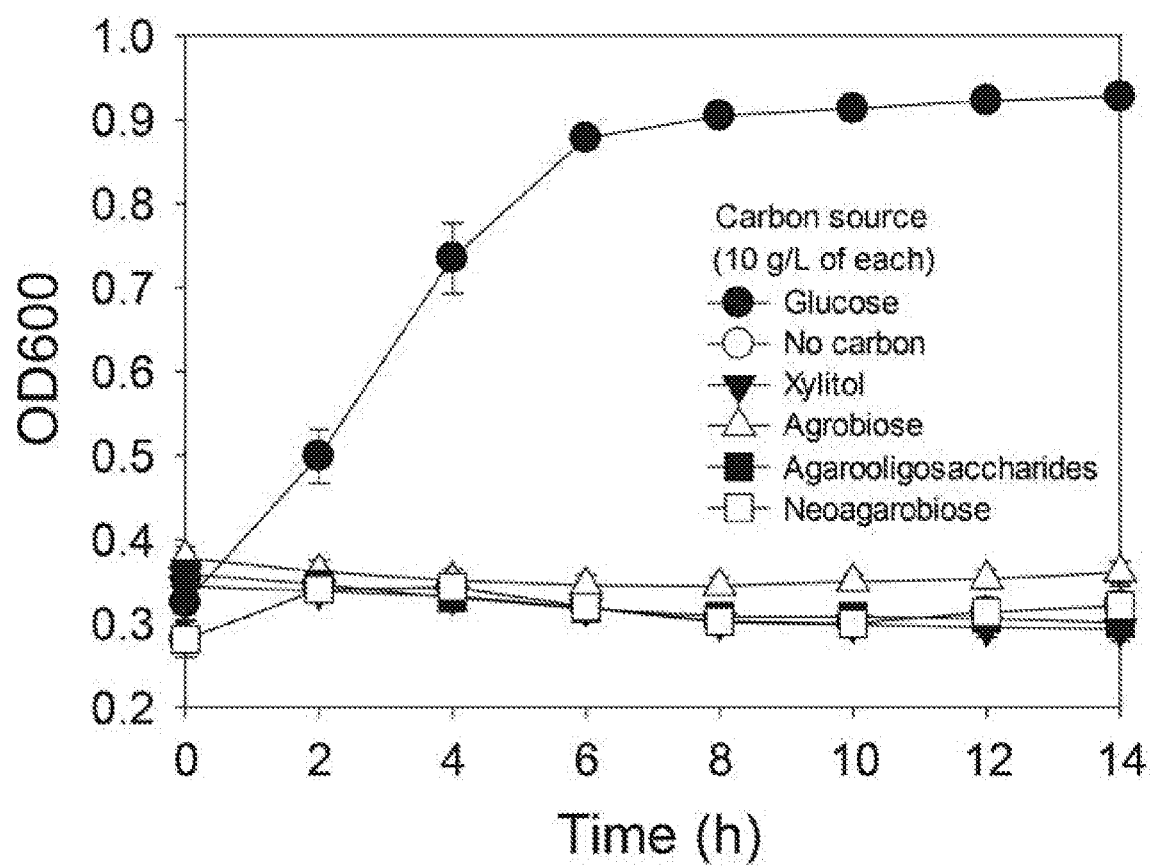
FIG. 1 illustrates an effect of a single carbon source on the growth of *Streptococcus mutans* in a minimal medium (substrate conditions: 10 g/L of glucose; No carbon; 10 g/L of xylitol; 10 g/L of agarobiose; 10 g/L of agarooligosaccharides (a mixture of oligosaccharides having degrees of polymerization of 2, 4, 6, and 8); and 10 g/L of neoagarobiose).
Figure 2A:
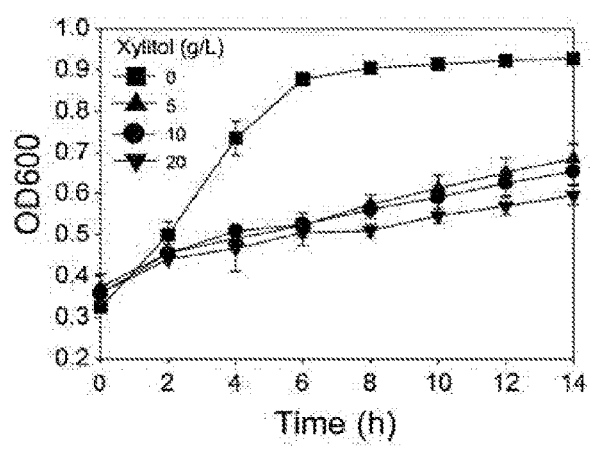
FIG. 2A, FIG. 2B, FIG. 2C and FIG. 2D illustrate concentration-dependent inhibitory effects of xylitol (FIG. 2A), agarobiose (FIG. 2B), agarooligosaccharides (FIG. 2C), and neoagarobiose (FIG. 2D) on the growth of *Streptococcus mutans* in a minimal medium containing 10 g/L of glucose.
Figure 2B:
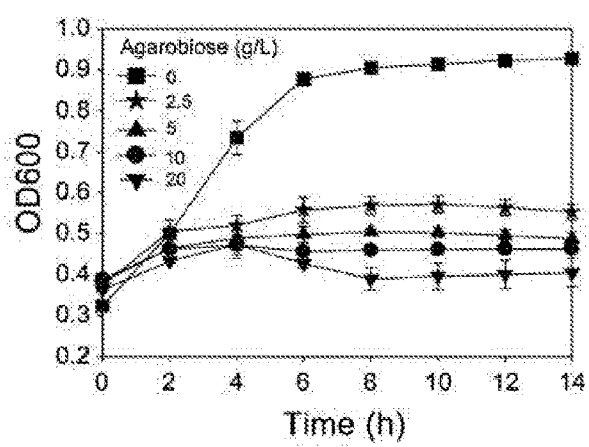
Figure 2C:
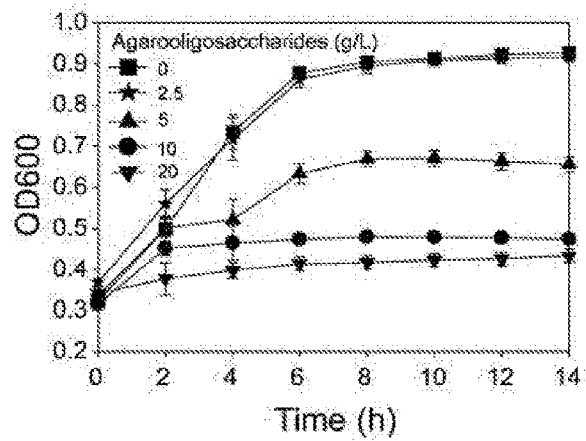
Figure 2D:
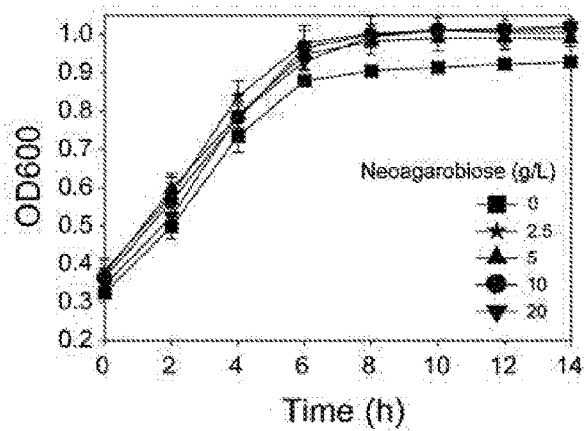
Figure 3A:
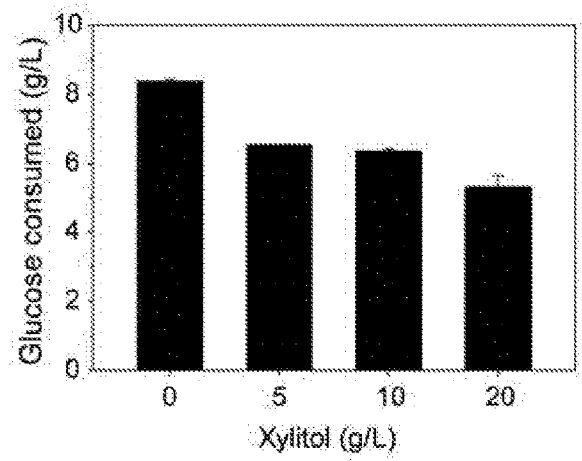
FIG. 3A, FIG. 3B, FIG. 3C and FIG. 3D illustrate results of analyzing consumed glucose when each of xylitol (FIG. 3A), agarobiose (FIG. 3B), agarooligosaccharides (FIG. 3C), and neoagarobiose (FIG. 3D) was added to a minimal medium containing 10 g/L of glucose at various concentrations.
Figure 3B:
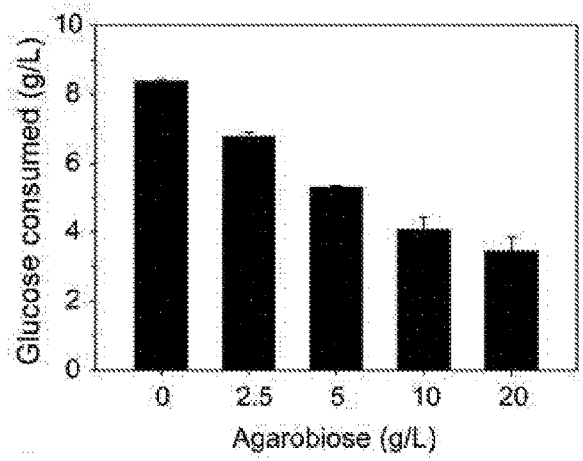
Figure 3C:
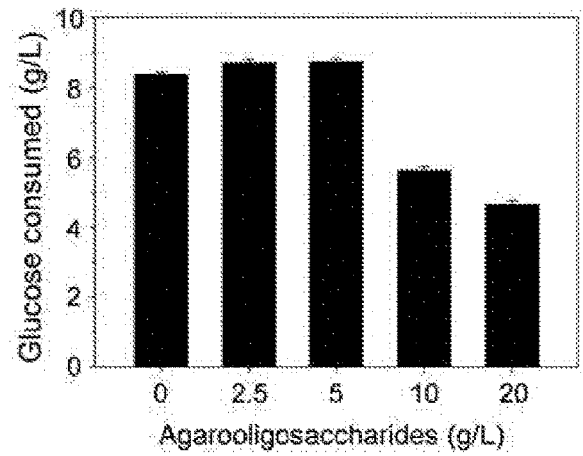
Figure 3D:
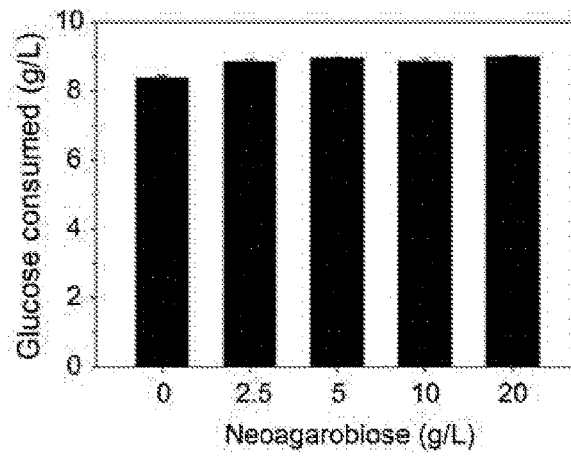
Figure 4A:
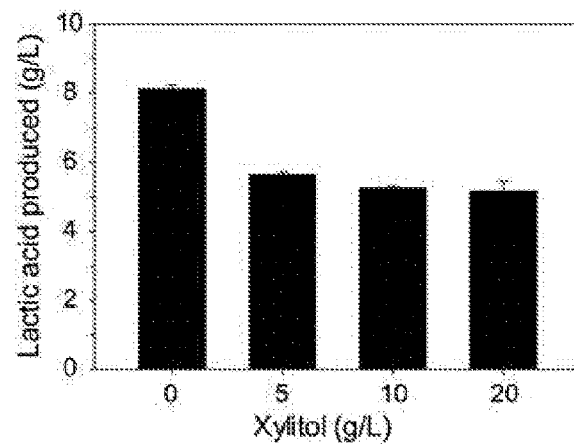
FIG. 4A, FIG. 4B, FIG. 4C and FIG. 4D illustrate results of analyzing produced lactic acid when each of xylitol (FIG. 4A), agarobiose (FIG. 4B), agarooligosaccharides (FIG. 4C), and neoagarobiose (FIG. 4D) was added to a minimal medium containing 10 g/L of glucose at various concentrations.
Figure 4B:
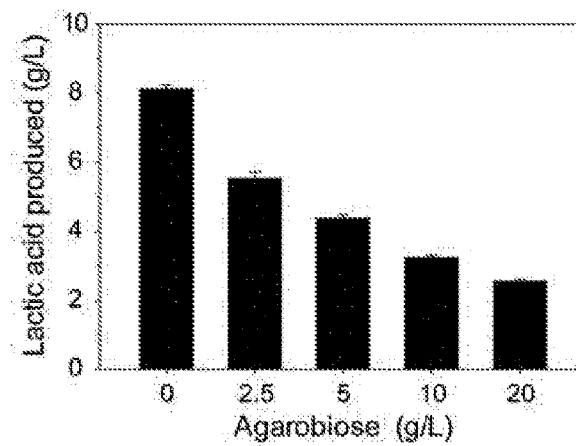
Figure 4C:
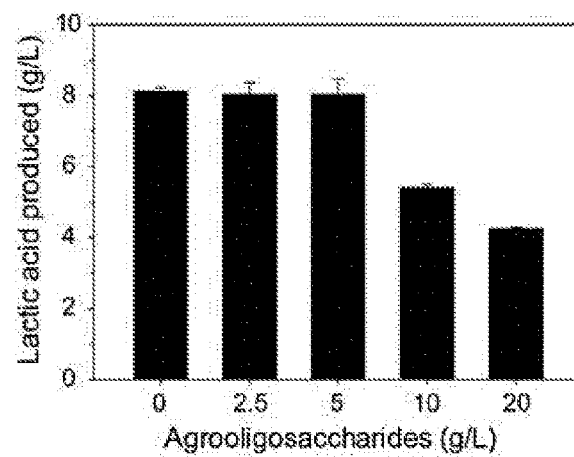
Figure 4D:
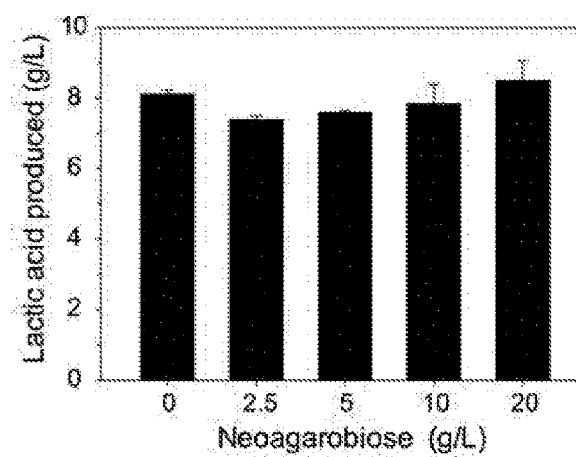

The inventors of the present invention produced agarooligosaccharides as a mixture of oligosaccharides having degrees of polymerization of 2, 4, 6, and 8 through acid hydrolysis of agarose, and then used the agarooligosaccharides as a carbon source for *Streptococcus mutans*. In addition, only an agarobiose disaccharide consisting of D-galactose and 3,6-anhydro-L-galactose was separated and purified and used as a carbon source for *Streptococcus mutans*. The inventors conducted research on an anticariogenic effect of agarobiose by observing whether agarobiose, which was accurately quantified using an agarobiose quantification method using HPLC, inhibited the growth and acid production of *Streptococcus mutans*. As controls, glucose, xylitol, and neoagarobiose were used as carbon sources to conduct comparative experiments.

As a result, it was verified that agarobiose and agarooligosaccharides of the present invention, which are capable of inhibiting cell growth, had an anticariogenic effect at a lower concentration than that of xylitol, which is known to be capable of inhibiting the growth of *Streptococcus mutans*. Red algae-derived agarooligosaccharides and agarobiose were produced through acid treatment and separation and purification processes, and then used as carbon sources to observe effects thereof on the growth of *Streptococcus mutans* by comparing with an effect of glucose, xylitol, or neoagarobiose as a carbon source on cell growth. In addition, agarobiose, agarooligosaccharides, xylitol, or neoagarobiose was added to a medium containing 10 g/L of glucose at various concentrations to observe the growth and acid production of *Streptococcus mutans* under mixed carbon source conditions. Through these experiments, it was first verified that purified agarobiose had a high inhibitory effect on the growth of *Streptococcus mutans* and an effect of inhibiting acid production at a lower concentration than that of commonly known xylitol. It was also verified that agarooligosaccharides had a stronger effect of inhibiting the growth and acid production of *Streptococcus mutans* than xylitol at a specific concentration or higher.

Therefore, the present invention provides a pharmaceutical composition for preventing or treating an oral disease, which includes one or more selected from the group consisting of agarobiose and agarooligosaccharides.

The present invention also provides a use of agarobiose or agarooligosaccharides for preparing a pharmaceutical composition for preventing or treating an oral disease.

The agarooligosaccharides may be obtained through acid hydrolysis of red algae biomass-derived agarose.

More particularly, the agarooligosaccharides may be obtained by reacting agarose with a 0.1% (w/v) to 5% (w/v) strong acid at 80° C. to 140° C. for 5 minutes to 30 minutes and adding a strong base to the resulting reaction product to be neutralized to a pH of 5 to 6.

The concentration of the strong acid may range from 0.1% (w/v) to 5% (w/v), more particularly 0.5% (w/v) to 2% (w/v).

The acid treatment reaction conditions may be a reaction between a 0.1% (w/v) to 5% (w/v) strong acid and agarose at 80° C. to 140° C. for 5 minutes to 30 minutes, more particularly a reaction between a 0.5% (w/v) to 2% (w/v) strong acid and agarose at 100° C. to 140° C. for 5 minutes to 20 minutes.

The strong acid may be phosphoric acid, sulfuric acid, hydrochloric acid, nitric acid, or the like. More particularly, the strong acid may be phosphoric acid.

The amount of the agarose used in strong acid treatment may be in a range of 10% (w/v) to 37% (w/v), particularly 15% (w/v) to 31% (w/v), and more particularly 16.8% (w/v) to 30.7% (w/v), with respect to a dry weight. When the amount of the agarose is within the above range, a liquefaction rate of 90%, 95%, or 98% or higher may be obtained. When the amount of the agarose is outside the above range, a substrate degradation rate may be significantly reduced.

A strong base is added to the strong acid-treated agarose to be neutralized to a pH of 5 to 6.

As the strong base, NaOH, KOH, $Ca(OH)_2$, $Ba(OH)_2$, or the like may be used, but the present invention is not limited thereto.

The agarooligosaccharides, which are obtained through the acid hydrolysis of agarose, may be a mixture of agarobiose, agarotetraose, agarohexaose, and agarooctaose.

The agarobiose used in the pharmaceutical composition of the present invention may be obtained by separating and purifying an acid hydrolysate of agarose through gel permeation chromatography.

The gel permeation chromatography may be Bio-gel P2 chromatography.

The pharmaceutical composition of the present invention may further include a pharmaceutically acceptable carrier.

The pharmaceutically acceptable carrier includes carriers and vehicles commonly used in the medical field, and examples thereof include, but are not limited to, ion exchange resins, alumina, aluminum stearate, lecithin, serum proteins (e.g., human serum albumin), buffer substances (e.g., phosphates, glycine, sorbic acid, potassium sorbate, and partial glyceride mixtures of saturated vegetable fatty acids), water, salts or electrolytes (e.g., protamine sulfate, disodium hydrogen phosphate, potassium hydrogen phosphate, sodium chloride, and zinc salts), colloidal silica, magnesium trisilicate, polyvinyl pyrrolidone, cellulose-based substrates, polyethylene glycol, sodium carboxymethylcellulose, polyarylate, waxes, polyethylene glycol, and wool fat.

In addition, the pharmaceutical composition of the present invention may further include, in addition to the above-described ingredients, a lubricant, a wetting agent, an emulsifying agent, a suspending agent, a preservative, or the like.

In one embodiment, the pharmaceutical composition according to the present invention may be formulated in the form of various preparations suitable for oral administration or parenteral administration.

Non-limiting examples of the preparations for oral administration include troches, lozenges, tablets, aqueous suspensions, oily suspensions, prepared powders, granules, emulsions, hard capsules, soft capsules, syrups, and elixirs.

To formulate the pharmaceutical composition of the present invention for oral administration, a binder such as lactose, saccharose, sorbitol, mannitol, starch, amylopectin, cellulose, gelatin, or the like; an excipient such as dicalcium phosphate or the like; a disintegrating agent such as corn starch, sweet potato starch, or the like; a lubricant such as magnesium stearate, calcium stearate, sodium stearyl fumarate, polyethylene glycol wax, or the like; or the like may be used, and a sweetener, a fragrance, syrup, or the like may also be used.

Furthermore, in the case of capsules, in addition to the above-mentioned substances, liquid carriers such as fatty oils may be further used.

Non-limiting examples of the preparations for parenteral administration include injections, suppositories, respiratory inhalation powders, aerosols for sprays, oral sprays, oral cleansers, toothpastes, ointments, powder for application, oils, and creams.

To formulate the pharmaceutical composition of the present invention for parenteral administration, sterilized aqueous solutions, non-aqueous solvents, suspensions, emulsions, freeze-dried preparations, agents for external application, or the like may be used, and as the non-aqueous solvents and the suspensions, propylene glycol, polyethylene glycol, a vegetable oil such as olive oil, an injectable ester such as ethyl oleate, or the like may be used.

In addition, more particularly, when the pharmaceutical composition of the present invention is formulated as an injection, the composition of the present invention may be mixed in water with a stabilizer or a buffer to be prepared into a solution or a suspension, which is then formulated into a unit dosage form such as an ampoule or a vial. In addition, when the pharmaceutical composition of the present invention is formulated as an aerosol, a propellant or the like may be mixed with an additive to disperse a water-dispersed concentrate or wet powder.

In addition, when the pharmaceutical composition of the present invention is formulated as an ointment, a cream, or the like, the pharmaceutical composition may be formulated using a carrier such as an animal oil, a vegetable oil, wax, paraffin, starch, tragacanth, cellulose derivatives, polyethylene glycol, silicone, bentonite, silica, talc, zinc oxide, or the like.

A pharmaceutically effective amount and an effective dose of the pharmaceutical position of the present invention may vary depending on the formulation method, administration method, administration time and/or administration route, or the like, and may vary according to various factors including the type and degree of the reaction to be achieved via administration of the pharmaceutical composition, the type of individual to which the composition is administrated, age, body weight, general health conditions, the symptoms or severity of diseases, gender, diet, excretion, drugs used simultaneously or at different times in the corresponding individual, ingredients of other compositions, and the like and similar factors well known in the medical field. The effective dose may be easily determined and prescribed for desired treatment by those of ordinary skill in the art. The pharmaceutical composition of the present invention may be administered once or several times a day. Thus, the dose is not intended to limit the scope of the present invention in any way.

The administration route and administration method of the pharmaceutical composition of the present invention may be independent of each other, the administration method is not particularly limited, and the administration route and the administration method may be an arbitrary administration route and administration route as long as they enable the pharmaceutical composition to reach the corresponding site. The pharmaceutical composition may be administered orally or parenterally.

The parenteral administration may be, for example, intravenous administration, intraperitoneal administration, intramuscular administration, transdermal administration, subcutaneous administration, or the like, and the composition may be applied or sprayed on a disease site, or inhaled, but the present invention is not limited thereto.

The pharmaceutical composition of the present invention may preferably be administered orally or via injection.

The term "prevention" as used herein means all actions that inhibit or delay the onset of an oral disease via administration of the pharmaceutical composition of the present invention to an individual.

The term "treatment" as used herein means all actions that alleviate or beneficially change symptoms of an oral disease via administration of the pharmaceutical composition of the present invention to an individual.

In the present invention, the oral disease is a concept encompassing all diseases occurring in the oral cavity regardless of symptoms thereof, and may include, for example, oral diseases mainly caused by oral pathogenic microorganisms such as *Streptococcus mutans, Porphyromonas gingivalis, Prevotella intermedia, Actinobacillus actinomycetemcomitans*, and pathogenic microorganisms belonging to the genus *Candida* such as *Candida albicans*, and the like, or oral diseases caused by oral immunity degradation. Non-limiting examples of the oral disease include dental caries, gingivitis, periodontitis, oral mucous ulcers, halitosis, and xerostomia.

The present invention also provides a method of preventing or treating an oral disease which includes administering the pharmaceutical composition for preventing or treating an oral disease to a subject.

As used herein, the term "subject" includes all animals including mammals including mice, livestock, humans, and the like.

In the method of preventing or treating an oral disease of the present invention, the description of dosage, administration route, administration method, and the like of the pharmaceutical composition is the same as described above in connection with the pharmaceutical composition of the present invention.

The present invention also provides an oral hygiene composition for preventing or alleviating an oral disease, which includes one or more selected from the group consisting of agarobiose and agarooligosaccharides.

In the present invention, the description of the agarobiose or agarooligosaccharides, the oral disease, and the prevention is the same as described above in connection with the pharmaceutical composition of the present invention.

In the present invention, the oral hygiene composition includes all types and preparations that may be used for hygiene of the oral cavity. Non-limiting examples of the oral hygiene composition may include toothpastes, mouthwashes, oral sprays, oral ointments, and gum.

The oral hygiene composition of the present invention may be formulated in the form of various preparations suitable for oral administration or parenteral administration to be used, and description related thereto is the same as described above in connection with the pharmaceutical composition of the present invention.

The term "alleviation" as used herein means all actions that decrease at least the degree of parameters related to conditions being treated, e.g., symptoms.

The present invention also provides a food composition for preventing or alleviating an oral disease, which includes one or more selected from the group consisting of agarobiose and agarooligosaccharides.

Here, the description of the agarobiose or agarooligosaccharides, the oral disease, and the prevention, and the alleviation is the same as described above in connection with the pharmaceutical composition of the present invention.

The food composition of the present invention is not particularly limited, and includes a health functional food composition.

The term "health functional food" as used herein refers to a food prepared by adding the agarobiose or agarooligosaccharides to food substances such as beverages, teas, condiments, gum, confectionaries, or the like, or a food prepared in the form of capsules, powders, suspensions, or the like, and refers to a food that imparts a specific health effect when ingested.

When the health functional food composition of the present invention is used as a food additive, the composition may be directly added or may be used in combination with other foods or food ingredients, and may be appropriately used according to a general method.

The type of the food is not particularly limited, and includes all foods in a general sense. Non-limiting examples of foods to which the material is applicable include meat, sausages, bread, chocolates, candies, snacks, confectionaries, pizza, ramen, other noodles, gum, dairy products including ice creams, various soups, beverages, teas, drinks, alcoholic beverages, and vitamin complexes.

When the health functional food composition of the present invention is a beverage composition, the beverage composition may include various flavor enhancers, natural carbohydrates, or the like as additional ingredients like general beverages. Non-limiting examples of the natural carbohydrates include monosaccharides such as glucose and fructose; disaccharides such as maltose and sucrose; natural sweeteners such as dextrin and cyclodextrin; and synthetic sweeteners such as saccharin and aspartame. A ratio of the added additional ingredients may be appropriately selected and determined by those of ordinary skill in the art.

In addition, the health functional food composition of the present invention may include various nutrients, vitamins, electrolytes, a flavoring agent, a colorant, pectic acid and a salt thereof, alginic acid and a salt thereof, organic acids, a protective colloidal thickening agent, a pH adjusting agent, a stabilizer, a preservative, glycerin, alcohols, carbonating agents used in carbonated beverages, or the like. In addition, the health functional food composition of the present invention may include pulp for preparing natural fruit juices, fruit beverages, vegetable beverages, or the like. These ingredients may be used alone or a combination of two or more of these ingredients may be used. A ratio of these additives may also be appropriately selected by those of ordinary skill in the art.

Hereinafter, the present invention will be described in further detail with reference to the following examples, but these examples are not intended to limit the scope of the present invention.

EXAMPLES

<Example 1> Production of Agarooligosaccharides Through Phosphoric Acid Hydrolysis of Agarose Agarose was dissolved in 2% phosphoric acid at a concentration of 30.7% (w/v) and a reaction was allowed to occur therebetween using a microwave digester at 110° C. for 10 minutes, and then the acid-hydrolyzed reaction product was neutralized using 5 M NaOH such that the reaction product had a pH of 5 to 6. The reaction product was lyophilized to obtain powder-type agarooligosaccharides.

<Example 2> Production of Neoagarobiose Using Aga16B and Aga50D

5% agarose was prepared using 200 mL of a 20 mM Tris-HCl buffer (pH 7.0) and dissolved in an autoclave at 121° C. for 10 minutes, and then 19.7 mg of Aga16B (see Korean Patent Application No. 2016-0006589) was added thereto in order to degrade the agarose, and a reaction was allowed to occur therein at 55° C. and 200 rpm for 12 hours, thereby obtaining neoagarotetraose and neoagarohexaose as reaction products. Each reaction product was allowed to react with 20 mg of Aga50D, which is an exo-type disaccharide-producing enzyme (see Korean Patent Application Publication No. 2010-0040438, published on Apr. 20, 2010) to decompose these reaction products, at 25° C. and 200 rpm, thereby obtaining neoagarobiose as a reaction product.

<Example 3> Separation and Purification Using Bio-Gel P2 Chromatography

To respectively separate and purify only agarobiose and neoagarobiose from the reaction products of Examples 1 and 2, Bio-gel P2 chromatography, which is gel permeation chromatography, was performed. Water was used as a mobile phase and a speed of the mobile phase was 0.1 mL/min. The volume of one fraction was 1 mL, and the sample consisting of a total of 100 fractions was analyzed through TLC, and then among these, only a fraction containing each of agarobiose and neoagarobiose was collected and lyophilized to thereby obtain powder-type agarobiose and powder-type neoagarobiose.

<Example 4> Analysis of Agarooligosaccharides Through HPLC and Quantification of Agarobiose and Neoagarobiose The agarooligosaccharides obtained according to Example 1 were analyzed by HPLC. The used column was KS-802 (Shodex), and each sample was analyzed at a column temperature of 80° C. and a flow rate of 5 mL/min. The used mobile phase was water.

As an analysis result, it was confirmed that the agarooligosaccharides of Example 1 mainly consisted of a mixture of oligosaccharides having degrees of polymerization of 2, 4, 6, and 8.

In addition, the agarobiose and neoagarobiose with high purity, which were produced according to Example 3, were analyzed by HPLC and quantified. The column, column temperature, flow rate, and mobile phase used in the analysis were the same as those used in the analysis of the agarooligosaccharides, i.e., KS-802 (Shodex), 80° C., 0.5 mL/min, and water, respectively.

<Example 5> Cell Culture Conditions

A strain used in the present experiment was *Streptococcus mutans* ATCC 25175. *Streptococcus mutans* ATCC 25175 was pre-cultured in a brain-heart infusion (BHI) medium for 8 hours, and was washed twice with a 2 mM potassium phosphate buffer, and then main-cultured in a minimal medium prepared with reference to a previously reported document (Fujiwara et al (1978) *Arch Oral Biol.* 23, 601-602) at 37° C. The minimal medium contains, in a 50 mM Tris-HCl buffer (pH 7.4), 2 g/L of L-glutamic acid, 0.2 g/L of cysteine hydrochloride, 0.9 g/L of L-leucine, 1 g/L of ammonium chloride, 3.5 g/L of potassium hydrogen phosphate, 1.5 g/L of potassium dihydrogen phosphate, 4.2 g/L of sodium hydrogen carbonate, 1.2 g/L of magnesium sulfate heptahydrate, 0.02 g/L of manganese chloride tetrahydrate, 0.02 g/L of iron sulfate heptahydrate, 0.6 g/L of sodium pyruvate, 1 mg/L of riboflavin, 0.5 mg/L of thiamine hydrochloride, 0.1 mg/L of biotin, 1 mg/L of nicotinic acid, 0.1 mg/L of p-aminobenzoic acid, 0.5 mg/L of calcium pantothenate, and 1 mg/L of pyridoxine hydrochloride.

<Example 6> Inhibitory Effect on Growth of *Streptococcus mutans* Under Single Carbon Source Condition To verify an effect of inhibiting the growth of *Streptococcus mutans* under a single carbon source condition, *Streptococcus mutans* were cultured in a minimal medium containing each of 10 g/L of agarobiose, agarooligosaccharides, glucose, xylitol, and neoagarobiose and a carbon source-free minimal medium. They were main-cultured using the method of Example 5 for 14 hours, and a degree of the cell growth was measured by measuring the absorbance of a culture solution at a wavelength of 600 nm every two hours.

As a result, the absorbance at 600 nm was measured as 0.927 8 at hours after *Streptococcus mutans* entered a stationary phase under a glucose condition. However, no growth of *Streptococcus mutans* was observed under conditions excluding glucose, i.e., in the case of agarobiose, agarooligosaccharides, xylitol, or neoagarobiose. Thus, it was confirmed that agarobiose, agarooligosaccharides, and neoagarobiose are non-fermentable sugars for *Streptococcus mutans* like xylitol, and had an effect of inhibiting the growth of *Streptococcus mutans* (see FIG. 1).

<Example 7> Effect of Inhibiting Growth of *Streptococcus mutans* Under Mixed Carbon Source Condition

*Streptococcus mutans* was cultured, using the method of Example 5, in 200 μl of a minimal medium containing 10 g/L of glucose and agarobiose, agarooligosaccharides, xylitol, or neoagarobiose at various concentrations in a 96-well plate, and growth inhibitory effects thereof were observed by measuring absorbance at a wavelength of 600 nm over time. The treated concentrations of agarobiose, agarooligosaccharides, xylitol, and neoagarobiose were between 0 g/L and 20 g/L.

The experimental results showed that there was no significant change in the growth of *Streptococcus mutans* under a condition of neoagarobiose up to a concentration of 20 g/L.

In contrast, in the case of agarobiose, inhibition of the growth of *Steptococcus mutans* was observed at a concentration of 2.5 g/L to 20 g/L. It was also confirmed that the effect of agarobiose on inhibiting the growth of *Streptococcus mutans* increased as a concentration thereof became higher. Also, in the case of xylitol, the growth of *Streptococcus mutans* was inhibited at a concentration of 5 g/L to 20 g/L and the growth inhibitory effect significantly increased as a concentration of xylitol became higher. However, when final absorbance values were compared after 14 hours of culture, a lower absorbance value was obtained at the same concentration under a condition of agarobiose than under a condition of xylitol. Thus, it was confirmed that the effect of agarobiose on inhibiting the growth of *Streptococcus mutans* was greater than that of xylitol (see FIG. 2A, FIG. 2B, FIG. 2C and FIG. 2D). Agarooligosaccharides also inhibited the growth of *Streptococcus mutans* at a concentration of 5 g/L to 20 g/L. The final absorbance at 5 g/L of agarooligosaccharide was similar to that at 5 g/L of xylitol, but absorbance values at concentrations of 10 g/L and 20 g/L were found to be lower under the agarooligosaccharide condition than under the xylitol condition. From these results, it was confirmed that the effect of agarooligosaccharides on inhibiting the growth of *Streptococcus mutans* was greater than that of xylitol (see FIG. 2A, FIG. 2B, FIG. 2C and FIG. 2D).

<Example 8> Effect of Inhibiting Acid Production of *Streptococcus mutans* Under Mixed Carbon Source Condition To confirm an effect of agarobiose, agarooligosaccharides, xylitol, or neoagarobiose on acid production of *Streptococcus mutans*, *Streptococcus mutans* were cultured, using the method of Example 5, in 200 μl of a minimal medium containing 10 g/L of glucose and 0 g/L, 2.5 g/L, 5 g/L, 10 g/L, or 20 g/L of agarobiose, agarooligosaccharides, or neoagarobiose, or 0 g/L, 5 g/L, 10 g/L, or 20 g/L of xylitol in a 96-well plate. After 14 hours, concentrations of extracellular glucose and produced lactic acid were measured by HPLC. A column used for HPLC analysis was Aminex HPX-87H. 0.01 N of sulfuric acid as a mobile phase was flowed at a rate of 0.5 mL/min and 65° C.

Under a condition of only glucose included as a carbon source, the absorbance value at 600 nm after 14 hours of culture was 0.927. At this time, glucose was consumed at 8.37 g/L, and the concentration of produced lactic acid was measured as 8.13 g/L (see FIG. 2A, FIG. 2B, FIG. 2C, FIG. 2D, FIG. 3A, FIG. 3B, FIG. 3C, FIG. 3D, FIG. 4A, FIG. 4B, FIG. 4C and FIG. 4D).

Under a condition of including 2.5 g/L of agarobiose in 10 g/L of glucose, the absorbance value after 14 hours of culture was 0.55, and the concentrations of consumed glucose and produced lactic acid were 6.78 g/L and 5.65 g/L, respectively. These are decreases of 19% and 32%, respectively, compared to the case of not including agarobiose. From these results, it was confirmed that the growth of *Streptococcus mutans* was inhibited by agarobiose from a concentration of 2.5 g/L. In addition, under a condition of 10 g/L of agarobiose, the amounts of consumed glucose and produced lactic acid were 4.05 g/L and 3.25 g/L, respectively, which correspond to decreases of 51.5% and 60%, respectively, as compared to a condition of 0 g/L of agarobiose. In addition, the amounts of consumed glucose and produced lactic acid under a condition of 20 g/L of agarobiose were reduced 58.76% and 68%, respectively, from which it was confirmed that the degree of acid production of

*Streptococcus mutans* was gradually reduced as the concentration of agarobiose increased (see FIG. 2A, FIG. 2B, FIG. 2C, FIG. 2D, FIG. 3A, FIG. 3B, FIG. 3C, FIG. 3D, FIG. 4A, FIG. 4B, FIG. 4C and FIG. 4D).

The amounts of consumed glucose and produced lactic acid after culturing for 14 hours under a condition of including 2.5 g/L or 5 g/L of agarooligosaccharides in 10 g/L of glucose did not show significant differences compared to an agarooligosaccharides-free condition. However, the amounts of consumed glucose and produced lactic acid under a condition of including 10 g/L of agarooligosaccharides were 5.63 g/L and 5.4 g/L, respectively, which correspond to decreases of 32% and 33.55%, respectively, as compared to an agarooligosaccharides-free condition. It was also confirmed that the amounts of consumed glucose and produced lactic acid under a condition of 20 g/L of agarooligosaccharides were reduced 44% and 47.7%, respectively (see FIG. 3A, FIG. 3B, FIG. 3C, FIG. 3D, FIG. 4A, FIG. 4B, FIG. 4C and FIG. 4D).

As a control, xylitol was added to 10 g/L of glucose at various concentrations. The amount of reduced lactic acid under a condition of including 5 g/L of xylitol was 30%, which was lower than that under a condition of 2.5 g/L of agarobiose, i.e., 32%. The absorbance value at 600 nm after culturing for 14 hours under a condition of adding 20 g/L of xylitol was found to be 0.595, which was higher than a condition of the same concentration of agarobiose. In addition, the amounts of consumed glucose and produced lactic acid were reduced 36.41% and 35%, respectively. From these results, it was confirmed that these were lower than those under a condition of the same concentration of agarobiose. When conditions of xylitol and agarooligosaccharides were compared, a decrease in the amount of consumed glucose under a condition of 10 g/L of agarooligosaccharides was 32%, which was higher than that under a condition of the same concentration of xylitol, i.e., 23.98%. At this time, a decrease in the amount of produced lactic acid under a condition of agarooligosaccharides was 33.55%, which was similar to that under a condition of xylitol, i.e., 35%. However, the amounts of consumed glucose and produced lactic acid under a condition of 20 g/L of agarooligosaccharide were reduced 44% and 47.7%, respectively, which correspond to greater decreases than those under a condition of xylitol, i.e., 36.41% and 35% (see FIG. 2A, FIG. 2B, FIG. 2C, FIG. 2D, FIG. 3A, FIG. 3B, FIG. 3C, FIG. 3D, FIG. 4A, FIG. 4B, FIG. 4C and FIG. 4D).

As in the case of agarobiose, neoagarobiose, which is a red algae-derived disaccharide, was added to 10 g/L of glucose at various concentrations and comparison was performed after culturing. As a result, it was confirmed that neoagarobiose did not exhibit significant differences in a final absorbance value, the amount of consumed glucose, and the amount of produced lactic acid up to a concentration of 20 g/L, as compared to the case of 0 g/L (see FIG. 3A, FIG. 3B, FIG. 3C, FIG. 3D, FIG. 4A, FIG. 4B, FIG. 4C and FIG. 4D).

From these results, it was confirmed that xylitol known as a sugar that prevents dental caries was unable to inhibit the growth and acid production of *Streptococcus mutans* as much as agarobiose at the same concentration. It was also confirmed that the degrees of inhibition of the growth and acid production of *Streptococcus mutans* under a condition of 5 g/L of agarobiose were greater than those under a condition of 10 g/L of xylitol. This indicates that the effect of agarobiose on inhibiting the growth and acid production of *Streptococcus mutans* is stronger at a lower concentration than that of xylitol. It was also confirmed that the effect of agarooligosaccharides on inhibiting the growth of *Streptococcus mutans* was similar to or stronger than that of xylitol at the same concentration. In contrast, neoagarobiose, which is a red algae-derived disaccharide like agarobiose, was unable to inhibit the growth and acid production of *Streptococcus mutans*. This indicates that, among red algae-derived disaccharides, only agarobiose has an effect of inhibiting the growth and acid production of *Streptococcus mutans*.

The present invention can be applied to the development field of oral hygiene products such as toothpastes, mouthwashes, oral sprays, and the like, foods such as gum, candies, and the like, and medicines.

What is claimed is:

1. A method for treating or alleviating an oral disease of a subject, comprising
    administering a therapeutically effective amount of agarobiose, agarooligosaccharides, or combination thereof to the subject,
    wherein the oral disease is any one selected from the group consisting of dental caries, gingivitis, periodontitis, oral mucous ulcers, halitosis, and xerostomia, and
    wherein the agarooligosaccharides are a mixture of agarobiose, agarotetraose, agarohexaose, and agarooctaose.

2. The method of claim 1, wherein the agarooligosaccharides are obtained from an acid hydrolysate of agarose.

3. The method of claim 1, wherein the agarobiose is obtained by separating and purifying an acid hydrolysate of agarose through gel permeation chromatography.

4. The method of claim 1,
    wherein the oral disease is caused by one or more oral microorganisms selected from the group consisting of *Streptococcus mutans, Porphyromonas gingivalis, Prevotella intermedia, Actinobacillus actinomycetemcomitans,* and *Candida albicans*.

* * * * *